United States Statutory Invention Registration [19]

[11] Reg. Number: H787

Collignon [43] Published: Jun. 5, 1990

[54] CARBOHYDRAZINIUM DINITRATE

[75] Inventor: Steven L. Collignon, Waldorf, Md.

[73] Assignee: The United States of America as represented by the Secretary of the Navy, Washington, D.C.

[21] Appl. No.: 379,034

[22] Filed: Jul. 12, 1989

[51] Int. Cl.[5] ..... C06B 47/08; D03D 23/00; C01B 21/12; C07C 133/02

[52] U.S. Cl. ..... 149/36; 149/109.6; 423/365; 564/34

[58] Field of Search ..... 149/36, 109.6; 423/365; 564/34

*Primary Examiner*—Edward A. Miller
*Assistant Examiner*—Ngollan T. Mai
*Attorney, Agent, or Firm*—K. E. Walden; Roger D. Johnson

[57] ABSTRACT

Carbohydrazinium dinitrate, which is formed by adding 2 moles of nitric acid ($HNO_3$) to each mole of carbohydrazide ($H_2NHNCONHNH_2$). This salt is useful as an oxidizer in slurry gun propellants.

5 Claims, No Drawings

---

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

CARBOHYDRAZINIUM DINITRATE

BACKGROUND OF THE INVENTION

This invention relates to propellants and more particularly to oxidizers for slurry gun propellants.

Slurry gun propellants should have high energy but cool burning characteristics. Energetic compounds with high oxygen content for oxidizing and high nitrogen content for cooling are desirable.

SUMMARY OF THE INVENTION

Accordingly, an object of this invention is to provide a new energetic compound.

Another object of this invention is to provide a new energetic oxidizer for slurry gun propellants.

A further object of this invention is to provide an energic oxidizer which contributes to the cool burn characteristics of a slurry gun propellant.

Yet another object of this invention is to provide a new method of preparing an energic oxidizer.

These and other objects of this invention are accomplished by providing carbohydrazinium dinitrate and a method of preparation.

DESCRIPTION OF THE PREFERRED EMBODIMENT

Carbohydrazinium dinitrate, $H_2NHNCONHNH_2.2HNO_3$, is the dinitric acid salt of carbohydrazide. The starting material carbohydrazide (Merck Index, 10th Ed., Compound No. 1787) is also known as carbonic dihydrazide (CAS Registry No. 497-18-7) and as carbazide (CRC Handbook of Chemistry and Physics, 59th Ed., Compound No. c136). Carbohydrazide has the formula $H_2NHNCONHNH_2$.

The carbohydrazinium dinitrate is prepared be mixing each mole of carbohydrazide with 2 moles of nitric acid in an aqueous solution at room temperature preferably a slight molar excess, about 5 to 10 percent of nitric acid is used. The concentration of nitric acid in the reaction solution is preferably from about 20 percent (see example) to about 70 percent, with from 20 to 50 percent being more preferred. The process is completed in less than one hour. The product carbohydrazinium dinitrate (a white solid) is isolated by removing the water and excess nitric acid. If the initial acid concentration was 50 percent greater, the water and excess acid are removed at room temperature in a desiccator under vacuum. If the initial nitric acid concentration was less than 50 percent, the water in excess of that which would have been required for a 50 percent acid solution may be removed at 35° C. to 45° C. under vacuum. The remaining water and excess acid are then removed at room temperature in a desiccator under vacuum. Attempts to remove all of the water at elevated (40° C.) temperature under vacuum resulted in a weight loss in the product. This is believed to be caused by a loss of nitric acid from the carbohydrazinium dinitrate.

Carbohydrazinium dinitrate is an energetic compound which is useful as an oxidizer in slurry gun propellants. In addition to its high oxygen content, carbohydrazinium dinitrate contains a substantial amount of nitrogen and therefore contributes to lower the burn temperatures for slurry propellants.

The general nature of the invention having been set forth, the following example is presented as a specific illustration thereof. It will be understood that the invention is not limited to this specific example but is susceptible to various modifications that will be recognized by one of ordinary skill in the art.

EXAMPLE

In a 250 round-bottom flask, 9.0 g (0.1 mole) of carbohydrazide was dissolved in 50 ml of water. While the solution was stirred, 19.8 g (0.22 mole) of 70% nitric acid was added After the addition was completed, the mixture was stirred for 1 hour at room temperature. Next, the excess nitric acid and approximately 40 ml of water was removed at 40° C. under vacuum. The remaining solution was then cooled to room temperature and placed in a desiccator under vacuum until dry. The product was 20.6 g of a white crystalline material. The theoretical yield for carbohydrazinium dinitrate is 21.6 g and for carbohydrazinium mononitrate it is only 15.3 g.

Elemental analysis gave C, 5.54; H, 3.81; N, 35.75; and O, 49.81. Theoretical values for carbohydrazinium dinitrate, $CH_8N_6O_7$, are C, 5.56; H, 3.73; N, 38.89; and O, 51.82. In contrast the theoretical values for carbohydrazinium mononitrate, $CH_7N_5O_4$, are C, 7.84; H, 4.61; N, 45.74; and O, 41.80.

The yield and elemental analysis establish that the product was the di-substitute nitric acid salt and not the mono-substituted salt.

Obvious numerous modifications and variations of the present invention are possible in light of the above teachings. It is therefore to be understood that, within the scope of the appended claims, the invention may be practiced otherwise than as specifically described.

What is claimed is:

1. Carbohydrazinium dinitrate.

2. A slurry gun propellant in which the improvement comprises using carbohydrazinium dinitrate as an oxidizer.

3. A process for preparing carbohydrazinium dinitrate comprising:

(1) contacting a mole of carbohydrazide with slightly more than 2 moles of nitric acid wherein the concentration of the nitric acid in water is from about 20 to about 70 percent; and (2) isolating the product carbohydrazinium dinitrate.

4. The process of claim 3 wherein the concentration of nitric acid in water is from 20 to 50 percent.

5. The process of claim 3 wherein the product carbohydrazinium is isolated in step (2) by removing the water and excess nitric acid at room temperature in a desiccator under vacuum.

* * * * *